United States Patent [19]
Bernardoni

[11] Patent Number: 5,370,604
[45] Date of Patent: Dec. 6, 1994

[54] KINESTHETIC ANKLE-FOOT ORTHOSIS

[76] Inventor: Gene P. Bernardoni, 641 W. Willow, Apt. 209, Chicago, Ill. 60614

[21] Appl. No.: 1,165

[22] Filed: Jan. 7, 1993

[51] Int. Cl.⁵ .................................. A61F 5/00
[52] U.S. Cl. ........................ 602/27; 264/223; 602/6; 602/10; 36/8.1
[58] Field of Search .................... 602/5–8, 602/10, 23, 27–29; 128/869, 882; 36/8.1, 11.5, 1, 25 R, 106; 264/222, 223, DIG. 30

[56] References Cited

U.S. PATENT DOCUMENTS

| | | | |
|---|---|---|---|
| 3,059,350 | 10/1962 | Price | 36/106 |
| 3,345,654 | 10/1967 | Noble | 602/28 X |
| 3,548,820 | 12/1970 | Bergen | 602/5 |
| 3,640,006 | 2/1972 | Kendrick | 36/8.1 |
| 3,800,376 | 4/1974 | Whyte | 602/10 |
| 3,916,886 | 11/1975 | Rogers | 602/28 |
| 3,976,059 | 8/1976 | Lonardo | 602/28 |
| 4,351,324 | 9/1982 | Bronkhorst | 602/27 |
| 4,525,940 | 7/1985 | Mochizuki | 36/8.1 |
| 5,154,695 | 10/1992 | Farris et al. | 602/27 |
| 5,197,942 | 3/1993 | Brady | 602/23 X |

FOREIGN PATENT DOCUMENTS

| | | | |
|---|---|---|---|
| 0937846 | 1/1956 | Germany | 602/27 |
| 8707498 | 12/1987 | WIPO | 602/27 |

OTHER PUBLICATIONS

Wu, Kent K., "Foot Orthoses: Principles and Clinical Applications," published by Williams & Wilkins, Baltimore, Md. (1990), pp. 110–111 and 130–131.

Primary Examiner—Richard J. Apley
Assistant Examiner—Linda C. M. Dvorak
Attorney, Agent, or Firm—Willian Brinks Hofer Gilson & Lione

[57] ABSTRACT

An orthosis to support the sole of a foot of a person comprising a support surface having a shape conforming substantially to the shape of the sole of the foot and the support surface comprises a first opening underlying a first portion of the sole of the foot.

57 Claims, 3 Drawing Sheets

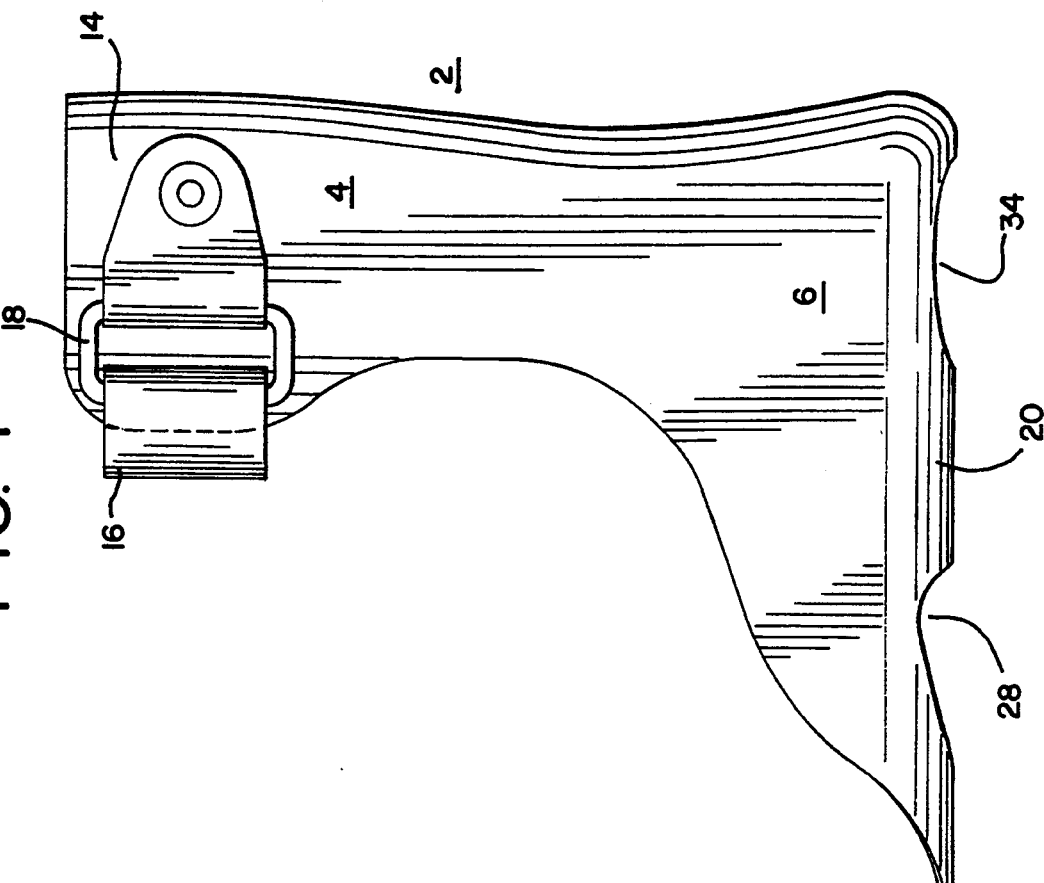
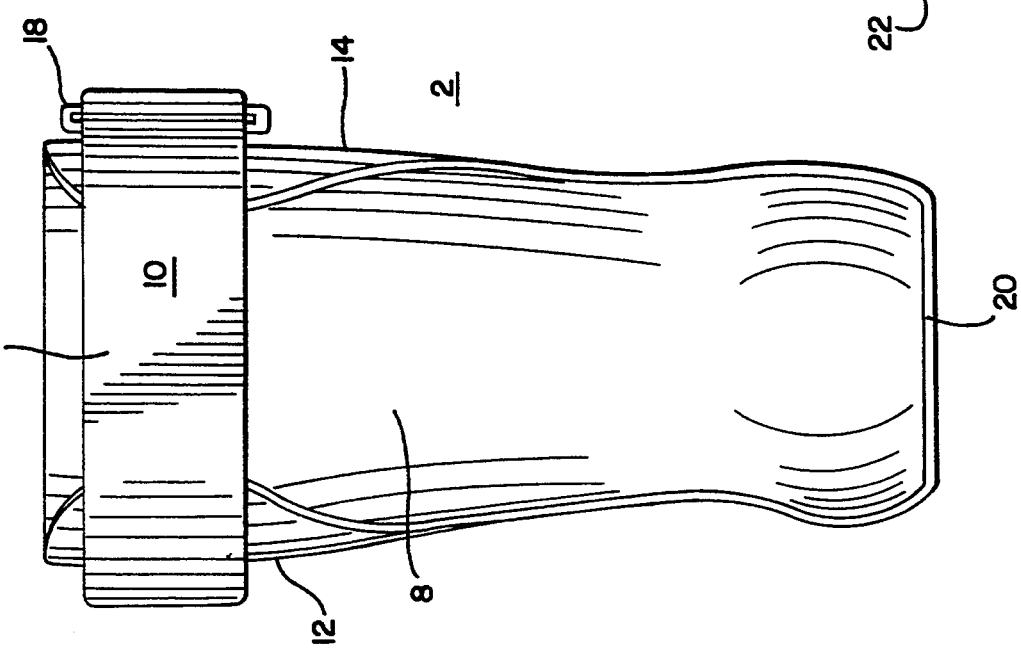

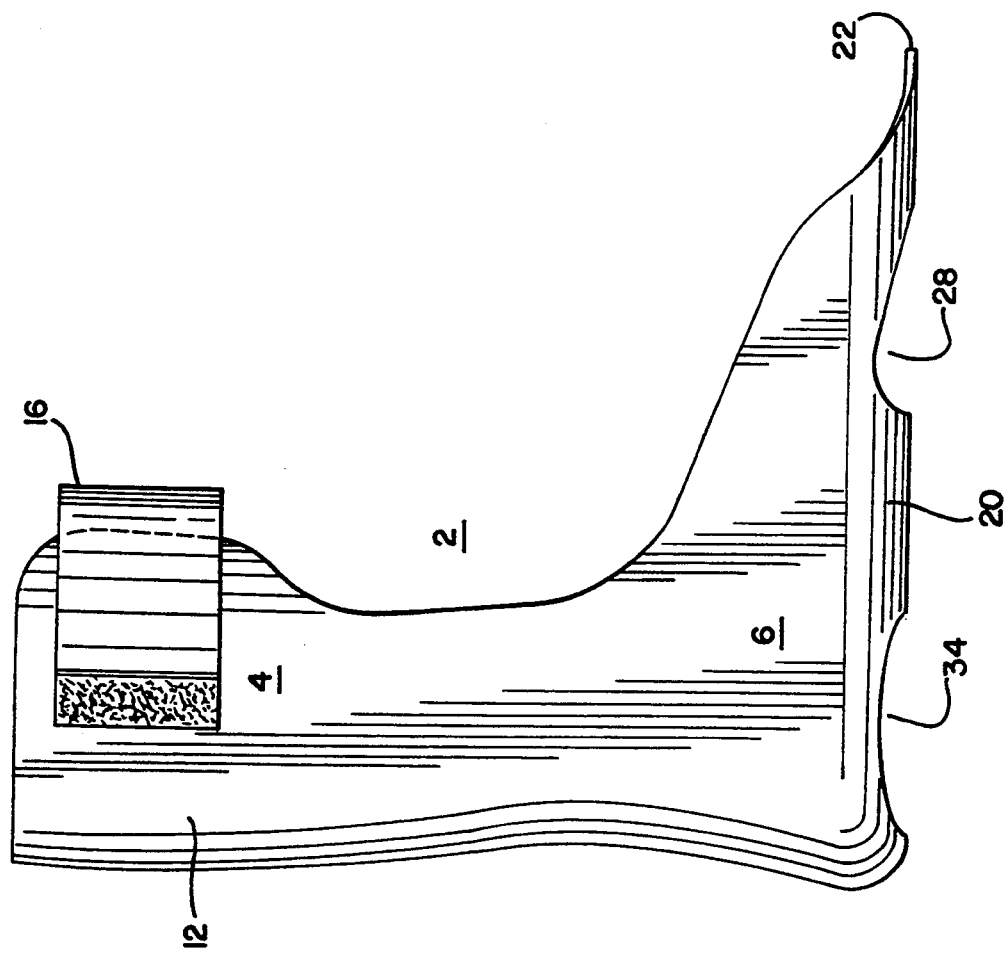
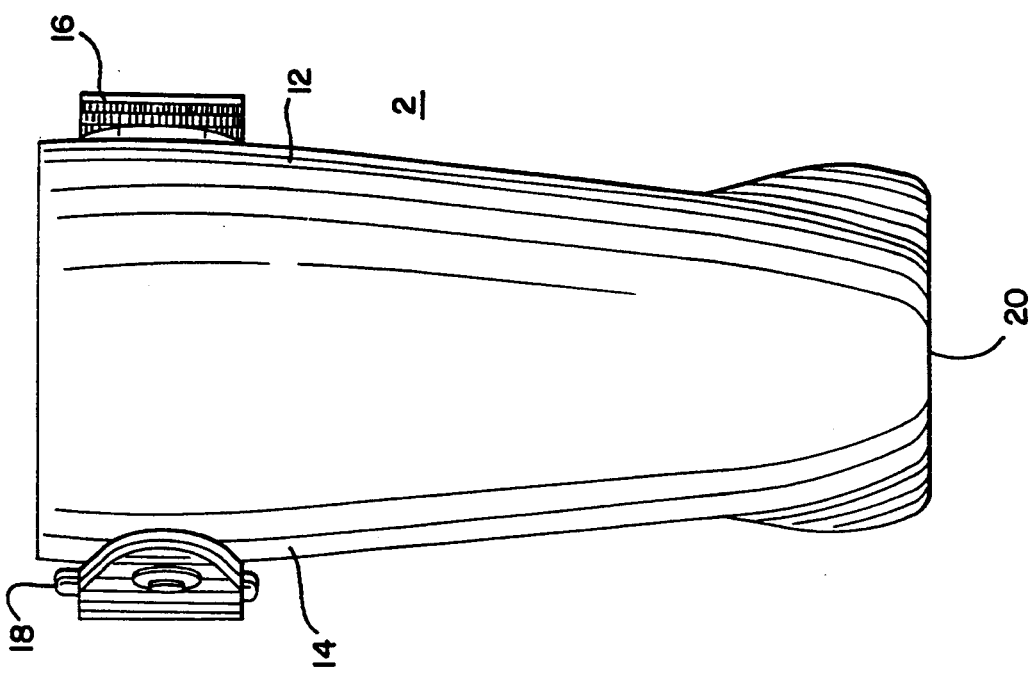

KINESTHETIC ANKLE-FOOT ORTHOSIS

FIELD OF THE INVENTION

The present invention is directed to the field of ankle-foot orthoses used to mechanically lift a foot of a person suffering from "drop foot."

BACKGROUND OF THE INVENTION

"Drop foot" is a frequently encountered condition in which a person is unable to lift a foot. Drop foot may be the result of nerve damage from spinal surgery, brain damage from cardiovascular accident (CVA) or "stroke", hereditary motor and sensory neuropathies, or neuromuscular disease, such as Dystrophia Myotonica. Any damage to the "motor unit" (i.e., muscle and nerves which activate the muscle) of the neuromuscular system related to the foot may cause drop foot.

The neuromuscular system of the foot comprises the pretibial muscles which are those muscles on the front of the leg and below the knee which lift the foot. The action of lifting the foot from a position substantially aligned with the lower leg to a position substantially perpendicular to the lower leg is known by the term "dorsiflexion." However, if the pretibial muscles are weak, a person will be unable to lift the foot as required in the swing phase of a gait. This inability to lift the foot may cause a person to trip, since the foot may make contact with the grounds during the downward swing of the leg.

A person may avoid having the foot contact the ground by lifting the entire leg higher, but this is not efficient in terms of energy expenditure. Another solution is to use a brace to mechanically lift the foot and give the person a more stable, energy efficient gait. This type of brace or "orthosis" is known as an Ankle-Foot Orthosis (AFO). Prior art AFO's comprise double metal uprights attached to the shoe or a thermoplastic rigid 90° brace made to fit inside of a shoe.

Drop foot may have other side effects such as a loss or diminishing of the sensation of touch. The sensation of touch includes the ability to feel a pin prick or pain and the ability to sense movement. Kinesthesia is the ability to sense the movement of muscles, tendons, and joints. In particular, proprioceptors are special receptor nerves which enable one to sense the movement of muscles, tendons, and joints. The proprioceptors are located in the subcutaneous tissue of the muscles, tendons, and joints and they respond to stimuli produced within the body. The proprioceptors allow one to know where one's foot or hand is in space without seeing them.

A human body relies on three systems for maintaining balance: the vestibular system, the visual system, and the somatic-sensory system or kinesthesia. It is possible to maintain balance with only two of the systems in operation. In the case of a foot, the foot normally contacts the floor and the three most important areas are: 1) the first metatarsal head; 2) the fifth metatarsal head; and 3) the calcaneus or heel. These three contact areas form a tripod in which the foot is supported and in which sensory feed-back is provided to maintain balance.

However, when drop foot causes a loss or reduction of kinesthesia, a person using prior art AFO's may only be able to maintain balance during a walk by looking at his or her feet. This is so because the prior art AFO's impose an extra barrier between the foot and the floor causing a decrease in kinesthesia.

Accordingly, it is an object of the present invention to provide an orthosis which provides improved kinesthesia for a wearer of an AFO.

It is another object of the present invention to provide an orthosis which may enable the wearer to reduce his or her dependence on walking aids for balance, such as canes or walkers.

It is another object of the present invention to produce a more stable gait and a more energy efficient gait during walking.

DETAILED DESCRIPTION OF DRAWINGS

FIG. 1 is a medial side view of an embodiment of the present invention;

FIG. 2 is a front or anterior view of the embodiment of FIG. 1;

FIG. 3 is a lateral side view of the embodiment of FIG. 1;

FIG. 4 is a posterior or back view of the embodiment of FIG. 1;

SUMMARY OF THE INVENTION

Figure 5:
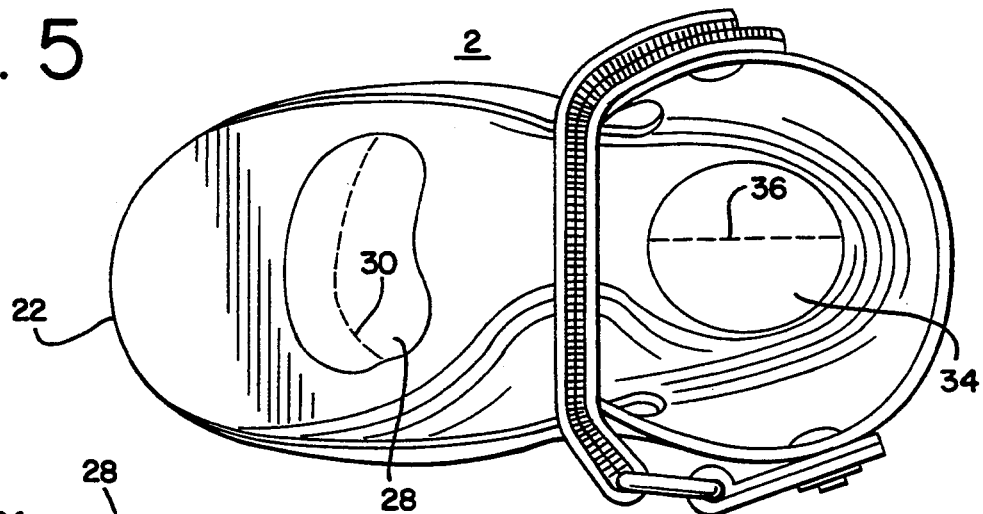
FIG. 5 is a top view of the embodiment of FIG. 1.

One embodiment of the present invention, an orthosis, is described which supports the sole of a foot of a person. The orthosis comprises a support surface having a shape conforming substantially to the shape of the sole of the foot and the support surface comprises a first opening underlying a first portion of the sole.

The present invention as described above provides the advantage that improved kinesthesia is provided to the wearer. The amount of improved kinesthesia is such that it may enable the wearer to reduce his or her dependence on walking aids and visual aids.

The present invention as described above advantageously produces a more stable and energy efficient gait during walking.

DETAILED DESCRIPTION OF AN EMBODIMENT OF THE INVENTION

The present invention is best understood upon viewing the embodiments illustrated in FIGS. 1-7, where like elements are denoted by like numerals. In FIGS. 1-6 an ankle-foot orthosis 2 according to an embodiment of the present invention is shown. The ankle-foot orthosis 2 is made of a single piece of a rigid material such as polypropylene having a thickness ranging from about 1/16" to about 3/16". As described below, the single piece of material is initially formed into a shape that substantially conforms with the exterior surface shape of the calf, ankle and foot of a patient or person. The ankle-foot orthosis 2 illustrated in FIGS. 1-6 is employed by having a person insert his or her foot into the orthosis so that the ankle and foot are positioned at a support position in which the ankle-foot orthosis 2 snugly conforms to the ankle and foot.

Ankle-foot orthosis 2 comprises an upper section 4 to support the calf and ankle of the patient and a bottom section 6 for supporting the foot of the patient. Upper section 4 extends from the top of the ankle-foot orthosis 2 to the top of the bottom section 6 which is located just below the malleoli.

From the anterior view of FIG. 2, the upper section 4 has a longitudinal-like opening 8 extending along the length of the ankle-foot orthosis 2. When the ankle-foot orthosis 2 is worn, a tight fit is insured by employing an attachment device 10 to attach those sections 12 and 14 of the upper section 4 located on opposite sides of the longitudinal-like opening 8. The attachment device 10 may consist of a proximal anterior strap 16 made of a hook and loop system and known by the trademark VELCRO and attached to section 12 by such well known devices such as a copper rivet located on one side of the longitudinal-like opening 8. The strap 16 is then threaded through a loop 18 attached to section 14 located on the other side of the longitudinal-like opening 8.

Below the upper section 4 is a bottom section 6 which is integrally connected to upper section 4. Preferably upper section 4 and bottom section 6 are made from the same continuous piece of material. Bottom section 6 has a support surface 20 having a shape conforming substantially to the shape of the sole of the foot of a person.

The shape of the support surface is such that it allows one or more portions of the sole of the foot to make contact with a floor when the ankle-foot orthosis 2 and the foot are supported on a floor.

Figure 6:
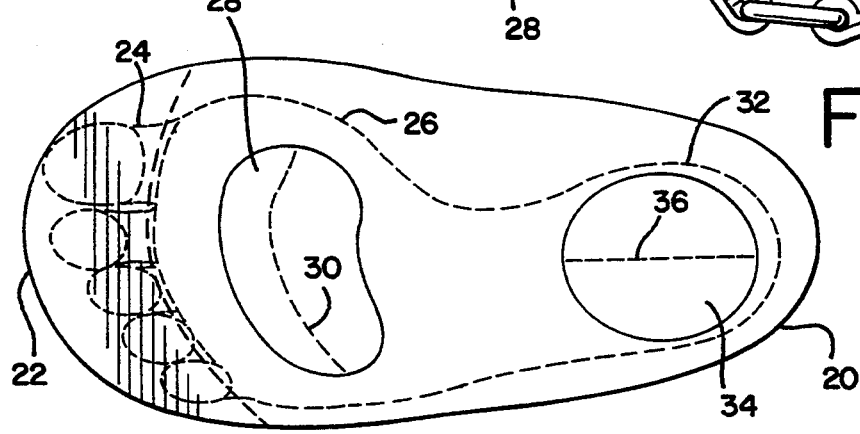
FIG. 6 is a bottom view of the embodiment of FIG. 1.

In the embodiment of FIGS. 1-6, the ankle-foot orthosis 2 provides contact of several portions of the sole with the floor. As seen in FIG. 6, ankle-foot orthosis 2 has a front edge 22 which is shaped so that a first portion 24 of the sole of the foot (dashed lines), extending from approximately distal to the metatarsalphalangeal joint line of the foot to the tip of the toes, lies on the support surface 20. Note that the front edge 22 may be positioned so that some of the first portion 24 of the sole extends past the front edge 22 (see dashed lines 22 of FIG. 6).

A second portion 26 of the sole makes contact with the floor via a first opening 28. Opening 28 is approximately kidney-shaped as shown in FIG. 6. It should be appreciated that other shapes for opening 28 are possible. The opening 28 is located and sized so that the portion of the sole corresponding to the first through fifth metatarsal heads (balls of the foot) makes contact with the floor. The opening 28 comprises a curved line 30 of bisection of the opening 28 (shown by dashed lines) substantially parallel with the metatarsalphalangeal joint line defined by the first through fifth metatarsals. The line 30 preferably coincides with the metatarsalphalangeal joint line. It is preferred that the line 30 approximately coincides with each of the first through fifth metatarsal heads. The size of opening 28 is chosen so as to maximize the surface area of the sole making contact with the floor while at the same time providing adequate support for the sole.

A third portion 32 of the sole makes contact with the floor via a second opening 34. Opening 34 is oval-like in shape and is located and sized so that the portion of the sole corresponding to the calcaneus or heel makes contact with the floor. It should be appreciated that other shapes for opening 34 are also possible. The opening 34 comprises a line of symmetry 36 (shown by dashed lines) substantially parallel with the midsagittal line of the sole. The line of symmetry 36 preferably coincides with the midsagittal line. It is preferred that one of the geometric centers of the oval-like opening approximately coincides with the calcaneus. The size of opening 34 is chosen so as to maximize the surface area of the sole making contact with the floor while at the same time providing adequate support for the sole.

Note that regardless of the thickness of the support surface 20, the edges of the front edge and the openings are tapered to make a smooth transition from the support surface 20 to the floor or shoe surface.

Figure 7:
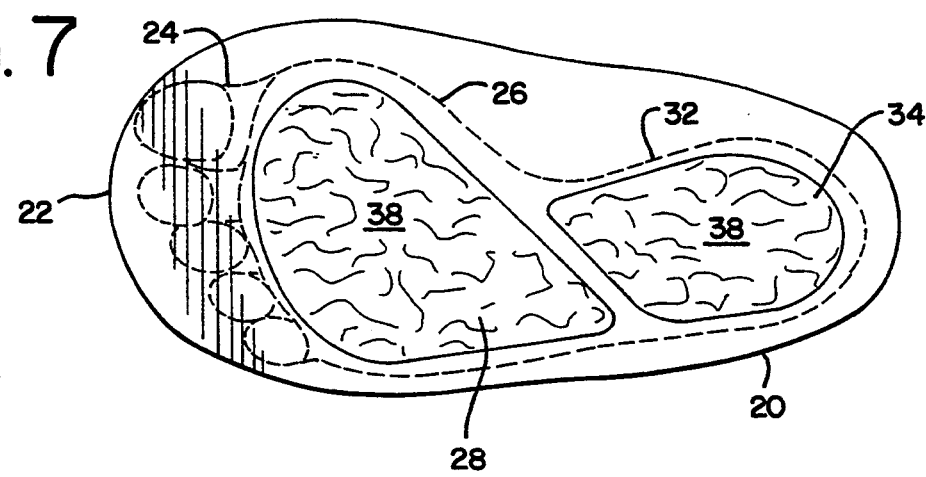
FIG. 7 is a bottom view of a second embodiment of the invention.

In another embodiment of the invention shown in FIG. 7, a cover 38 may be attached to the side of the support surface 20 facing the sole of the foot so that one or more of openings 28 and 36 are covered. The cover 38 prevents the foot from falling too much through the opening by acting as a sling. Thus, the cover 38 allows for openings 28 and 36 to be larger than the corresponding openings 28 and 36 of the embodiment of FIGS. 1-6, because the cover 38 itself prevents too much of the foot from coming through the openings. Consequently, the larger openings 28 and 36 allow for more foot contact and, thus, greater stability. Note that the size and shape of the openings may be varied along with the separation between the openings. This embodiment also provides improved protection of the foot from the outside elements. Furthermore, the cover 38 may be used to prevent a person having an allergic reaction to the plastic. It is preferred that the cover 38 comprises leather and is attached to the support surface 20 by such well-known ways as gluing.

Fabrication of the embodiments of the invention shown in FIGS. 1-7 employs a process similar to that described on pages 110-111 and 130-131 of "Foot Orthosis: Principals and Clinical Applications," by Kent K. Wu (published 1990). Accordingly, fabrication of the embodiments of the present invention requires a positive Plaster-of-Paris model of the foot and ankle to be made in a well-known manner.

In particular, a negative impression of the foot and ankle is manufactured by applying skin-tight plaster cast from just below the knee to the end of the toes. While holding the subtalar joint in a neutral position and the forefoot in pronation, wet plaster is molded around the heel, the foot arches, the metatarsal head region, and the sulcus between the toes and the foot. A rubber tube is placed longitudinally on the dorsal aspect of the foot and ankle before the plaster bandages are wrapped over the tube and the ankle and foot. The rubber tube provides for more ease in removing the cast.

When the cast starts to harden, a cast saw splits the cast longitudinally over the rubber tube allowing the foot to be withdrawn through the longitudinal opening. Once the foot is withdrawn, the two edges of the longitudinal opening are allowed to reapproximate their original position and are held there by adhesive tape. When the cast hardens a negative model of the foot is produced.

A positive model of the foot is produced by lubricating the interior of the negative model and then pouring liquid plaster into the negative model. When the liquid plaster is fully solidified, the negative model can be opened up revealing a plaster positive model or replica of the ankle and foot. Irregularities on the plantar aspect of the positive model are smoothed off, and the ankle-foot replica is now ready to be used for making a custom made ankle-foot orthosis.

Note that a small pipe is inserted in the negative model of the ankle and foot while the liquid plaster is poured into the negative model. The pipe facilitates the vacuum-forming process to be described hereafter. The pipe is connected to a vacuum source to form a vacuum to be used to form a heated thermoplastic such as polypropylene over the model. A sheet of approximately ⅛" to 3/16" polypropylene is cut having a size slightly larger than the plantar surface of the positive replica to compensate for the shrinkage of the plastic during the heating, molding, and curing process. The sheet is then heated in an oven. When the sheet has become soft and pliable, it is tightly wrapped around the positive model and the vacuum suction pipe. The vacuum from the pipe results in the soft thermoplastic sheet being tightly drawn around the positive model of the foot and ankle to form a plastic model. The plastic model comprises an upper section conforming substantially with the shape of the ankle for supporting the ankle and a bottom section conforming substantially with the shape of the foot for supporting the foot.

After the plastic sheet cools, the positive model is removed and the various openings and edges previously mentioned are cut out of or trimmed from the plastic to form the final product, as described previously. The places to cut and trim the openings and edges may be marked on the positive model. Any rough edges of the orthosis are then smoothed off with a grinder until it fits perfectly on the sole of the negative model. Note that the front edge 22 and the edges of openings 28 and 34 are tapered to a small thickness.

Next a D-ring and strap made of a hook and loop system and known by the trademark VELCRO are attached to the orthosis for holding the orthosis to the lower leg. The patient is then fitted with the finished ankle-foot orthosis and the orthosis is adjusted until it fits the patient's lower leg properly.

In another variation of the above-described manufacturing process, a cover may be positioned and attached over one or more of the openings. Attachment is preferably accomplished by using such attachment devices as glue.

While the invention has been described with relation to certain presently preferred embodiments, it is understood that the invention as expressed in the claims is not limited to those described preferred embodiments. Those with skill in this art will recognize other modifications of the invention which will still fall within the scope of the invention, as expressed in the accompanying claims.

I claim:

1. An orthosis to rigidly support the sole of a foot of a person comprising:
   a rigid support surface having a shape sized and configured substantially to the shape of the sole of the foot and said support surface including a first opening of sufficient size to underlie and to allow either the metatarsal heads or the heel of the sole to extend therethrough.

2. The orthosis of claim 1, comprising a cover positioned over said first opening.

3. The orthosis of claim 1, wherein said first opening is adapted to underlie the heel of the sole.

4. The orthosis of claim 3, wherein said first opening is oval in shape.

5. The orthosis of claim 4, wherein said first opening comprises a line of symmetry adapted to be positionable substantially parallel to the midsagittal line of the sole.

6. The orthosis of claim 1, wherein said first opening is adapted to underlie the metatarsal heads of the sole.

7. The orthosis of claim 6, wherein said first opening has a kidney shape.

8. The orthosis of claim 7, wherein a curved line of bisection of said kidney shape is approximately located at the first metatarsal head.

9. The orthosis of claim 7, wherein a curved line of bisection of said kidney shape is approximately located at the fifth metatarsal head.

10. The orthosis of claim 8, wherein said curved line of bisection of said kidney shape is approximately located at the fifth metatarsal head.

11. The orthosis of claim 1, wherein said support surface comprises a second opening of sufficient size to underlie and to allow the other of said metatarsal heads or heel of the sole to extend therethrough.

12. The orthosis of claim 11, comprising a cover positioned over said first opening and said second opening.

13. The orthosis of claim 11, wherein said second opening is oval-like in shape.

14. The orthosis of claim 13, wherein said second opening comprises a line of symmetry adapted to be positionable substantially parallel with the midsagittal line of the sole.

15. The orthosis of claim 11, wherein said second opening is adapted to underlie the heel of the sole.

16. The orthosis of claim 1, wherein said rigid support surface comprises a rigid plastic.

17. The orthosis of claim 16, wherein said rigid plastic comprises polypropylene.

18. An orthosis to rigidly support the sole of a foot of a person comprising:
    a rigid support surface having a shape sized and configured substantially to the shape of the sole of the foot, wherein said shape of said support surface is adapted such that a first portion of the sole extends beyond said support surface and said support surface includes a first opening of sufficient size to underlie and to allow either the metatarsal heads or the heel of the sole to extend therethrough.

19. The orthosis of claim 18, wherein said first opening is adapted to underlie the heel of the sole.

20. The orthosis of claim 19, wherein said first opening is oval-like in shape.

21. The orthosis of claim 20, wherein said first opening comprises a line of symmetry adapted to be positionable substantially parallel with the midsagittal line of the sole.

22. The orthosis of claim 18, wherein said first opening is adapted to underlie the metatarsal heads of the sole.

23. The orthosis of claim 22, wherein said first opening has a kidney shape.

24. The orthosis of claim 23, wherein a curved line of bisection of said kidney shape is approximately located at the first metatarsal head.

25. The orthosis of claim 23, wherein a curved line of bisection of said kidney shape is approximately located at the fifth metatarsal head.

26. The orthosis of claim 24, wherein said curved line of bisection of said kidney shape is approximately located at the fifth metatarsal head.

27. The orthosis of claim 18, wherein said support surface comprises a second opening of sufficient size to underlie and to allow the other of said metatarsal heads or heel of the sole to extend therethrough.

28. The orthosis of claim 27, wherein said second opening is oval-like in shape.

29. The orthosis of claim 26, wherein said second opening comprises a line of symmetry adapted to be positionable substantially parallel with the midsagittal line of the sole.

30. The orthosis of claim 27, wherein said second opening is adapted to underlie the heel of the sole.

31. The orthosis of claim 18, comprising a cover positioned over said first opening.

32. The orthosis of claim 18, wherein said support surface comprises a rigid plastic.

33. The orthosis of claim 32, wherein said rigid plastic comprises polypropylene.

34. An orthosis to rigidly support the ankle and sole of a foot of a person comprising:
   an upper section for supporting the ankle;
   a bottom section for supporting the foot, wherein said bottom section comprises:
   a rigid support surface having a shape sized and configured substantially to the shape of the sole of the foot and said support surface including a first opening of sufficient size to underlie and to allow either the metatarsal heads or the heel of the sole extend therethrough.

35. The orthosis of claim 34, wherein said support surface comprises a second opening of sufficient size to underlie and to allow the other of said metatarsal heads or the heel of the sole to extend therethrough.

36. The orthosis of claim 34, wherein said rigid support surface comprises a rigid plastic.

37. The orthosis of claim 36, wherein said rigid plastic comprises polypropylene.

38. An orthosis to support the ankle and sole of a foot of a person comprising:
   an upper section for supporting the ankle;
   a bottom section for supporting the foot, wherein said bottom section comprises:
   a support surface having a shape sized and configured substantially to the shape of the sole of the foot, wherein said shape of said support surface is such that a first portion of the sole extends beyond said support surface and said support surface includes a first opening of sufficient size to underlie a and to allow either the metatarsal heads or the heel of the sole to extend therethrough.

39. An orthosis to rigidly support the sole of a foot of a person comprising:
   a first side wall;
   a second side wall;
   a rigid support surface attached to said first and second side walls and having a shape sized and configured substantially to the shape of the sole of the foot and said support surface including a first opening having sufficient size to underlie and to allow either the metatarsal heads or the heel of the sole to extend therethrough; and
   wherein said first and second side walls are each attached to said rigid support surface and extend in a direction approximately perpendicular to said rigid support surface.

40. The orthosis of claim 39, wherein said first opening is adapted to underlie the heel of the sole.

41. The orthosis of claim 40, wherein said first opening is oval in shape.

42. The orthosis of claim 41, wherein said first opening comprises a line of symmetry adapted to be positionable substantially parallel to the midsagittal line of the sole.

43. The orthosis of claim 40, wherein said first opening has a kidney shape.

44. The orthosis of claim 39, wherein said support surface further includes a second opening of sufficient size to underlie and to allow the other of said metatarsal heads or heel of the sole to extend therethrough.

45. The orthosis of claim 44, wherein said second opening is oval in shape.

46. The orthosis of claim 39, comprising an adjustable attachment device for attaching said first side wall to said second side wall so as to attach the foot to the orthosis.

47. The orthosis of claim 46, wherein said attachment device comprises a strap.

48. A method of using an orthosis for rigidly supporting the sole of a foot of a person, comprising the steps of:
   providing a contact surface;
   providing a rigid support surface atop said contact surface, wherein said rigid support surface has a shape sized and configured substantially to the shape of the sole of the foot and said support surface including a first opening adapted to underlie a first portion of the sole; and
   placing the foot upon said rigid support surface, wherein a portion of the foot extends through said first opening so as to make direct contact with said contact surface, so that the person feels the portion of the foot touching the contact surface resulting in improved kinesthesia and balance when the person stands or walks.

49. The method of claim 48, wherein said placing step comprises extending the heel of the foot through said first opening so as to make direct contact with said contact surface.

50. The method of claim 48, wherein said placing step comprises extending the first metatarsal of the foot through said first opening so as to make direct contact with said contact surface.

51. The method of claim 50, wherein said placing step comprises extending the fifth metatarsal of the foot through said first opening so as to make direct contact with said contact surface.

52. The method of claim 48, wherein said first opening is oval in shape.

53. The method of claim 48, wherein said first opening has a kidney shape.

54. The method of claim 48, further comprising the step of the person walking on the walking surface while the foot is upon the support surface.

55. The method of claim 48, wherein said support surface includes a second opening adapted to underlie a second portion of the sole, said method further comprising the step of:
   extending a second portion of the foot through said second opening so as to make direct contact with said contact surface, so that the person feels the second portion of the foot touching the contact surface resulting in improved kinesthesia and balance when the person stands or walks.

56. The method of claim 55, wherein said second opening is oval in shape.

57. The method of claim 55, further comprising the step of the person walking on the walking surface while the foot is upon the support surface.

* * * * *

UNITED STATES PATENT AND TRADEMARK OFFICE
CERTIFICATE OF CORRECTION

PATENT NO. : 5,370,604
DATED : December 6, 1994
INVENTOR(S) : Gene P. Bernardoni It is certified that error appears in the above-indentified patent and that said Letters Patent is hereby corrected as shown below:

IN THE CLAIMS

Column 6:
    In claim 13, line 2, delete "oval-like" and substitute --oval--.

In claim 20, line 2, delete "oval-like" and substitute --oval--.

In claim 28, line 2, delete "oval-like" and substitute --oval--.

In claim 29, line 1, delete "26" and substitute --28--.

Column 7:
    In claim 34, line 10, after "sole" insert --to--.

In claim 38, line 11, delete "a".

Signed and Sealed this

Twentieth Day of August, 1996

Attest:

BRUCE LEHMAN

Attesting Officer     Commissioner of Patents and Trademarks